(12) United States Patent
Eggers et al.

(10) Patent No.: US 6,322,561 B1
(45) Date of Patent: Nov. 27, 2001

(54) PIVOT SCREW FOR BIPOLAR SURGICAL INSTRUMENTS

(75) Inventors: Philip Eggers, Dublin; Andrew Eggers, Ostrander, both of OH (US); Peter Wenzler, Frittlingen (DE)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/504,136

(22) Filed: Feb. 15, 2000

Related U.S. Application Data

(62) Division of application No. 09/107,205, filed on Jun. 29, 1998, now Pat. No. 6,053,914.

(51) Int. Cl.[7] .................................................. A61B 18/18
(52) U.S. Cl. .............................. 606/41; 606/48; 606/51; 606/52; 606/174; 606/208
(58) Field of Search .................. 606/41, 46, 47, 606/48, 49, 50, 51, 52, 32, 174, 208; 607/96, 98, 99

(56) References Cited

U.S. PATENT DOCUMENTS

| | | | |
|---|---|---|---|
| 5,601,189 | * | 2/1997 | Roshdy ................................. 206/363 |
| 5,649,958 | | 7/1997 | Grimm et al. . |
| 5,697,949 | | 12/1997 | Giurtino et al. . |
| 5,921,984 | | 7/1999 | Sutcu et al. . |
| 5,976,132 | * | 11/1999 | Morris ................................... 606/49 |

* cited by examiner

Primary Examiner—Linda C. M. Dvorak
Assistant Examiner—R Kearney
(74) Attorney, Agent, or Firm—Scully, Scott, Murphy, & Pressor

(57) ABSTRACT

A bipolar electrosurgical instrument having an improved pivot screw design is disclosed. The bipolar electrosurgical instrument has a first half which has a first pivot surface and a first bore. The first bore has a first stepped portion and an elongated portion proximate to the first pivot surface. A second half has a second pivot surface and a second bore having a second stepped portion. An insulating material is disposed on the first pivot surface and the elongated portion of the first bore. A first insert having a third bore in which the third bore has first threads is disposed in the second bore and prevented from entering the first bore by the second stepped portion. A second insert having a fourth bore is disposed in the second bore between the second stepped portion and the first insert and prevented from entering the first bore by the second stepped portion. Lastly, a pivot screw having a head and a second thread is disposed in the first, second, and third bores such that the head is prevented from entering the second bore by the first stepped portion and where the second thread passes through the first, second, and fourth bores, into the third bore engaging with the first thread whereby the first half is fastened to the second half for sliding contact between the first and second pivot surfaces. This arrangement leads to a bipolar instrument which greatly decreases the possibility of current leakage between instrument halves.

10 Claims, 10 Drawing Sheets

PIVOT SCREW FOR BIPOLAR SURGICAL INSTRUMENTS

This patent application is a divisional patent application of parent patent application Ser. No. 09/107,205, filed Jun. 29, 1998 now U.S. Pat. No. 6,053,914.

BACKGROUND OF THE INVENTION

1. Field of the Invention

The field of art to which this invention relates is bipolar surgical instruments, in particular, an improved pivot screw design for bipolar surgical instruments.

2. Description of the Related Art

A technique used extensively in both open and endoscopic surgery is the controlling of bleeding using bipolar electrosurgical instrumentation. The control of bleeding during surgery accounts for a major portion of the time involved in surgery. In particular, bleeding that occurs when tissue is incised or severed can obscure the surgeon's vision, prolong the operation, and adversely effect the precision of cutting. Blood loss from surgical cutting may require blood infusion, thereby increasing the risk of harm to the patient.

Hemostatic electrosurgical techniques are known in the art for reducing bleeding from incised tissue prior to, during, and subsequent to incision. Electrosurgical cutting and coagulating instruments are used to perform such techniques. These instruments can be of a reusable type (which require cleaning and disinfecting or sterilizing before each use) or disposable (which are disposed of after a single use). Each type includes both monopolar and bipolar variations having at least one electrode. Radio frequency (RF) energy is conducted through this electrode to either a remote conductive body-plate (known as a grounding pad) in the case of monopolar instruments, or to a second, closely spaced conductive electrode in the case of bipolar instruments. In monopolar instruments electrical current travels from the electrode through the patient's body to the grounding pad. Bipolar instruments are typically connected to both poles of an electrosurgical generator, therefore current flow is typically limited to tissue adjacent to the working end of the bipolar instrument (where the two electrodes are located).

Bipolar electrosurgical instruments typically comprise two halves which pivot about a pivot means such as a pivot screw. However, pins and rivets are also utilized as the pivot means. Each halve comprises an electrode which needs to be electrically isolated from the other half. Isolation of the instrument halves is typically achieved by either coating a metallic pivot screw with an insulating material or fabricating the pivot screw entirely from an insulating material. In addition, surfaces of the two halves which are in sliding contact with each other are insulated, typically by coating the common surfaces with an insulating material, such as alumina oxide.

FIGS. 1 and 2 illustrate a bipolar surgical instrument of the prior art, and generally referred to as reference numeral 100. The bipolar surgical instrument 100 typically comprises a first and a 30 second half 102, 104. Each half has a distal end 102a, 104a at which an end effector, such as scissor blades, are disposed. Each half also has a proximal end 102b, 104b at which an actuating means is disposed, such as finger loops 106, 108. Each instrument half comprises an electrode, whereby RF energy of differing polarity is supplied to each half through connector posts 110, 112 disposed at the proximal end 102b, 104b of the instrument halves 102, 104. The two halves 102, 104 engage in sliding contact at first and second pivot surfaces 114, 116 and are fastened together at the pivot surfaces 114, 116 by a fastening means, typically a pivot screw 118 disposed in a first and second bore 120, 122. The pivot screw has a head 118a and a first threaded portion 118b. The first bore 120 being in the first half 102, the second bore 122 being in the second half 104 and opposing the first bore 120.

To electrically isolate the two halves from each other, a layer of insulating material 124 is disposed between the first and second halves at their sliding surfaces. If the screw 118 is a conductive material, such as aluminum, it is further coated with an insulating material to electrically isolate the two instrument halves from each other. Additionally, the instrument is typically coated with an insulating material 126 in all portions other than the end effectors so as to insulate a user from electrical shock.

As can be seen in FIG. 2, the second bore 122 typically has a second threaded portion 128, whereby the first bore 120 is typically sized as a through hole to accommodate easy passage of the first threaded portion 118b of the pivot screw 118 but which captures the head 118a of the pivot screw 118. The screw 118 is disposed through the first bore 120 where the first threaded portion 118b engages with the second threaded portion 130 of the second bore 122 to provide a positive locking of the two halves.

Coated aluminum screws with an anodized coating are typically used in the art. While they have the advantage of being able to withstand the physical abuse typically encountered during surgery and processing (cleaning, disinfecting, and sterilizing), they suffer from a number of disadvantages. The most serious of which is the loss of portions of the coating due to rubbing contact between mating surfaces. Because the screw head 118a moves relative to the instrument half 102, the screw coating is subject to wear. An uncoated portion of the screw or a chipped portion of the screw's insulating coating can lead to an eventual shorting across the screw and between the instrument halves. This will result in a very low resistance between instrument halves. Consequently, the voltage maintained between the instrument halves will not be sufficient to effect adequate hemostasis. The greater the worn portion is in size, the more significant the degradation of the hemostasis performance.

Ceramic coated screws, such as alumina oxide coated on aluminum, are also used as the pivot screw in a bipolar surgical instrument. However, ceramics are brittle and prone to chipping. As discussed, chipping of the insulating coating can lead to poor or inadequate hemostasis. Furthermore, ceramic coated screws do not easily thread into a mating female thread because of its high coefficient of friction. Impregnating, the screw with a material having a lower coefficient of friction, typically a polymer, helps with the latter problem. However, the impregnation does little to solve the former problem and adds significant costs to the fabrication of the screws.

Pivot screws fabricated entirely from ceramic or an impregnated ceramic also have their drawbacks. Ceramic screws are brittle and susceptible to failure when subjected to external forces caused by mishandling of the instrument. For instance, dropping the instrument from an instrument table to a hard operating room floor can result in the fracturing of the ceramic pivot screw, resulting in instrument failure.

Plastic screws have also been contemplated as pivot screws in bipolar surgical instruments. Like ceramic screws, plastic screws cannot withstand the impact stresses associated with mishandling the instrument, such as when the instrument is dropped onto a hard surface. Additionally, plastic screws cannot withstand expected torque levels experienced during normal use which is needed to adequately hold the two instrument halves together. Not only do plastic pivot screws suffer from being susceptible to failure from impact and torsional stresses, they can also fail electrically. Plastic screws have been found to fail from carbon tracking due to the high voltages used in bipolar electrosurgical instruments. Typically, the voltages run as high as 1,500 volts (peak to peak). At such elevated voltages, plastic screws can burn and/or melt causing catastrophic failure of the bipolar instrument.

Besides electrical conduction between instrument halves due to worn or chipped insulation on the screw 118, electrical conduction can occur directly between instrument halves 102,104 as a result of exposed portions of the pivot surfaces 114,116. If the insulating material 124 disposed on one or both of the pivot surfaces 114, 116 is chipped around or near the pivot screw 118, poor hemostasis will result. Such a chipped area, leaves portions of the pivot surfaces 114,116 exposed. An insulating material 124 having a chipped area 132 is shown in FIG. 2. When the gap associated with the chipped area 132 is filled with an electrically conductive liquid (e.g., isotonic saline or blood) and the resulting exposed pivot surface areas are sufficiently large while the gap spacing is small, the resistance between the instrument halves 102, 104 can become small. As a consequence, there is low voltage between the instrument halves resulting in poor hemostasis until the conductive liquid boils away. If the chipped portion 132 is around the first and/or second bores then the exposed area can be come much larger and the associated resistance much lower.

Accordingly, there is a need in the art for electrosurgical instruments having an improved pivot screw design which can withstand the physical and electrical rigors associated with bipolar instrumentation, and which also provide an effective isolation between electrodes.

Furthermore, there is also a need in the art for electrosurgical instruments having an improved pivot screw design in which the likelihood of electrical conduction between instrument halves great enough to influence effective hemostasis is decreased.

SUMMARY OF THE INVENTION

Therefore, it is an object of the present invention to provide a pivot screw design for electrosurgical instruments in which the likelihood of electrical conduction between instrument halves is decreased.

It is yet a further object of the present invention to provide a pivot screw design for electrosurgical instruments in which the above objective is fulfilled without sacrificing the mechanical strength of the pivot screw.

It is still yet another object of the present invention to provide a pivot screw design for electrosurgical instruments in which the likelihood of electrical conduction between instrument halves great enough to influence effective hemostasis is decreased.

Accordingly, a first embodiment of a bipolar electrosurgical instrument having an improved pivot screw design is provided. The instrument has a first half which acts as a first electrode of a first polarity. The first half also has a first pivot surface and a first bore. The first bore has a first stepped portion. The instrument also has a second half which acts as a second electrode of a second polarity. The second half has a second pivot surface in sliding contact with the first pivot surface and a second bore having a second stepped portion. The second bore is aligned with the first bore. An insulating material is disposed on one of the first and second pivot surfaces for electrically isolating the first half from the second half. An insert of a certain cross-sectional profile and having a first insulating coating, and a third bore is also provided. The third bore further has first threads. The insert is disposed in the second bore and prevented from entering the first bore by the second stepped portion. Lastly, a pivot screw having a head and a second thread is provided. The pivot screw is disposed in the first and second bores such that the head is prevented from entering the second bore by the first stepped portion and where the second thread passes through the first and second bores into the third bore engaging with the first thread whereby the first half is fastened to the second half for sliding contact therewith along the first and second pivot surfaces.

A variation of the first embodiment of the bipolar electrosurgical instrument is also provided in which a second insert is disposed in the second bore between the second stepped portion and the first insert.

A second embodiment of the bipolar electrosurgical instrument having an improved pivot screw design is also provided. The instrument having a first half which acts as a first electrode of a first polarity. The first half has a first pivot surface and a first bore. The first bore having a stepped portion, an elongated portion proximate to the first pivot surface. The instrument also has a second half which acts as a second electrode of a second polarity. The second half has a second pivot surface in sliding contact with the first pivot surface and a second bore having a first thread. The second bore is aligned with the first bore. Also provided is an insulating material disposed on the first pivot surface and the elongated portion of the first bore for electrically isolating the first half from the second half and for increasing the length of the possible conductive path between the first and second halves. Lastly, a pivot screw having a head and a second thread is provided. The pivot screw is disposed in the first and second bores such that the head is prevented from entering the second bore by the first stepped portion and where the second thread passes through the first and second bores engaging with the first thread whereby the first half is fastened to the second half for sliding contact therewith along the first and second pivot surfaces.

First and second variations of the second embodiment are provided in which the second embodiment is combined with the first embodiment and variation of the first embodiment, respectively.

BRIEF DESCRIPTION OF THE DRAWINGS

These and other features, and advantages of the instruments and methods of the present invention will become better understood with regard to the following description, appended claims, and accompanying drawings where:

DETAILED DESCRIPTION OF THE PREFERRED EMBODIMENTS

Figure 1:
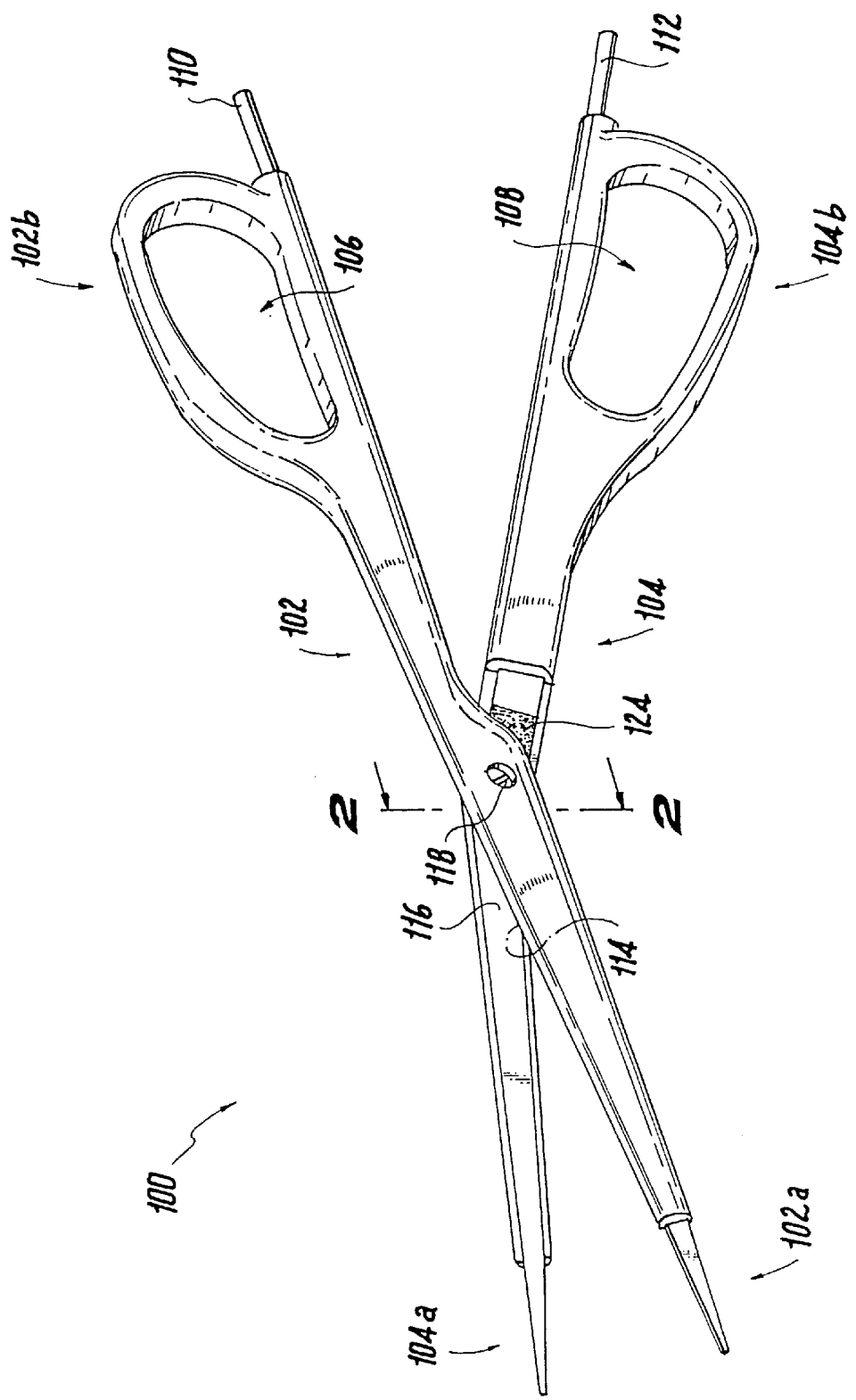
FIG. 1 illustrates a front view of a bipolar electrosurgical instrument of the prior art.
Figure 2:
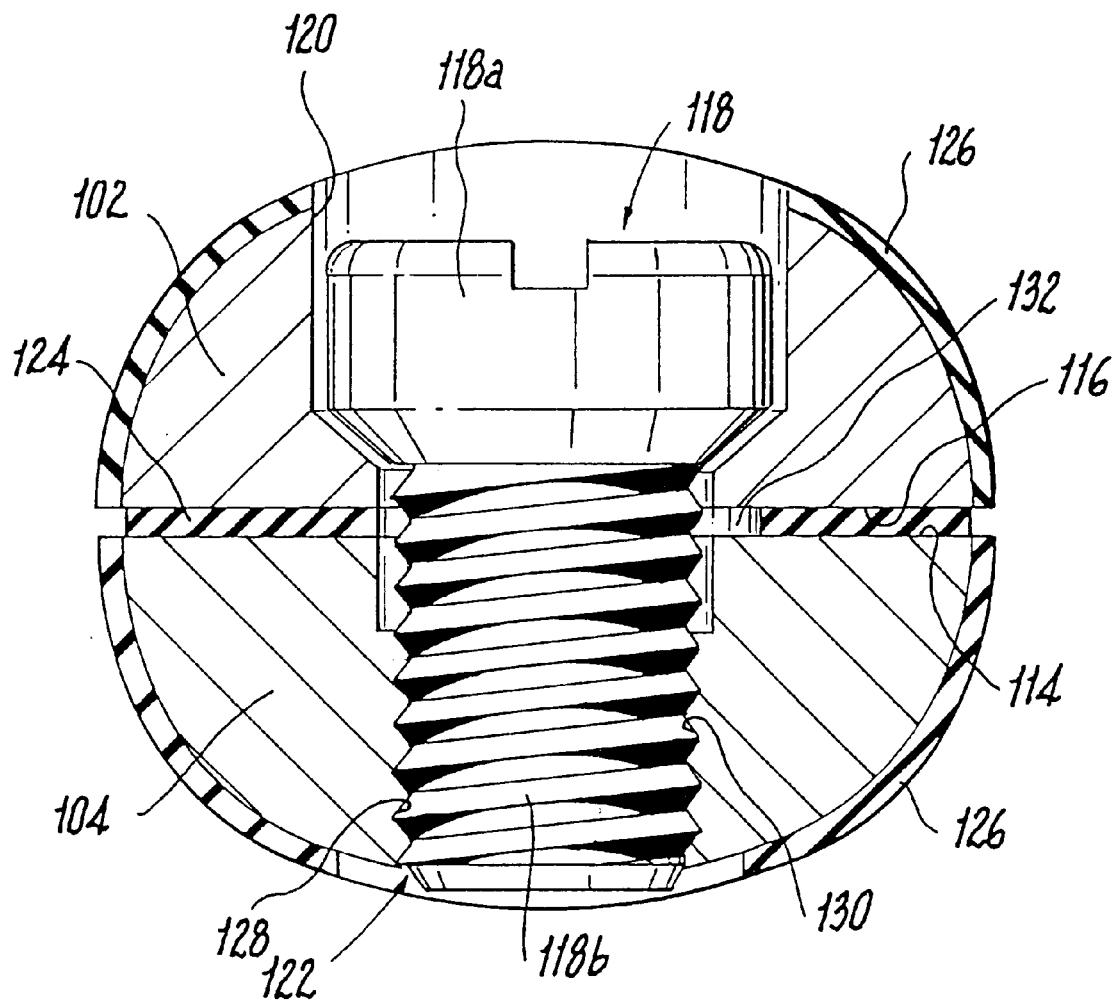
FIG. 2 illustrates a sectional view of the electrosurgical instrument of FIG. 1 as taken along line 2—2.
Figure 3:
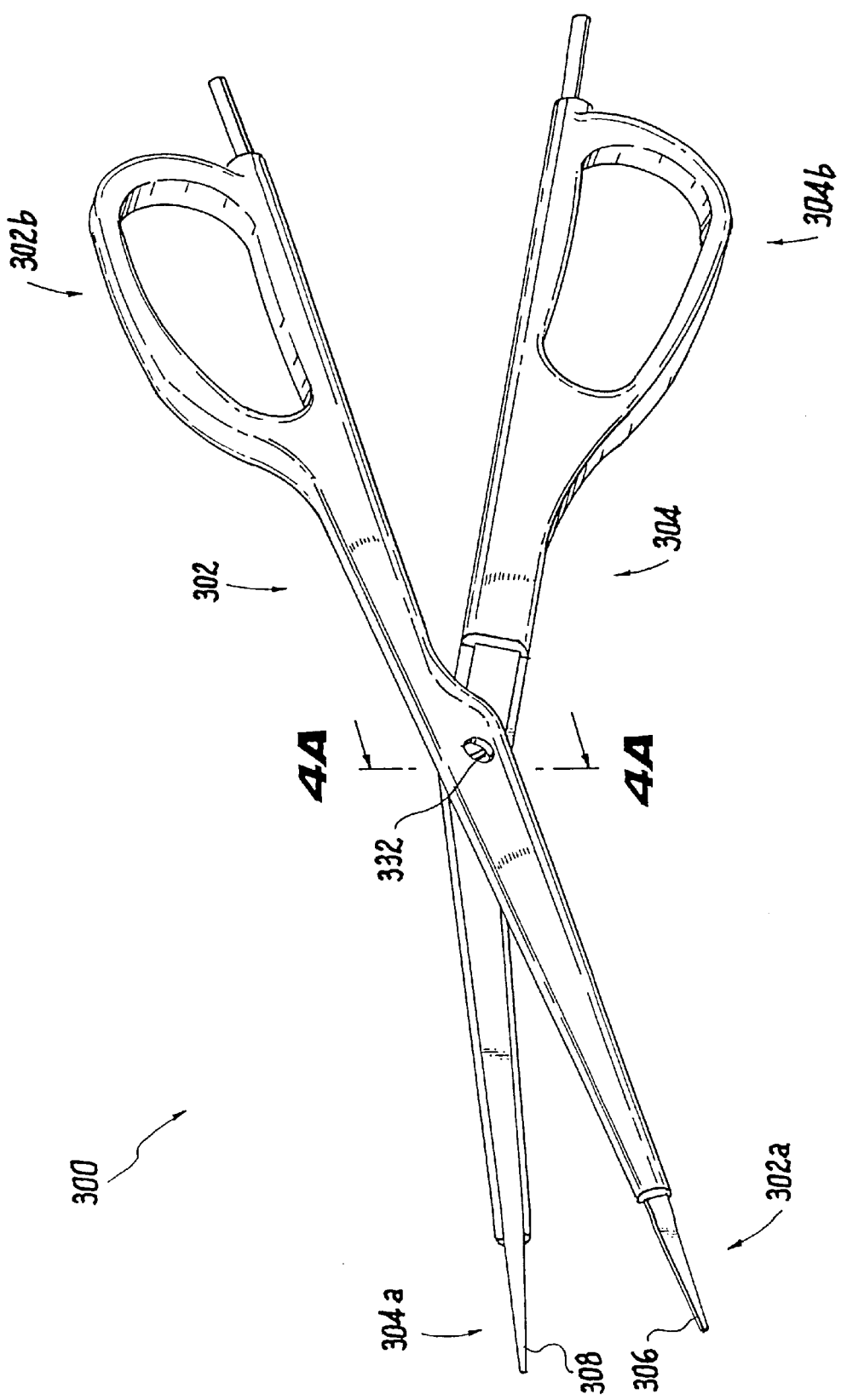
FIG. 3 illustrates a front view of a bipolar electrosurgical instrument of the present invention.
Figure 4A:
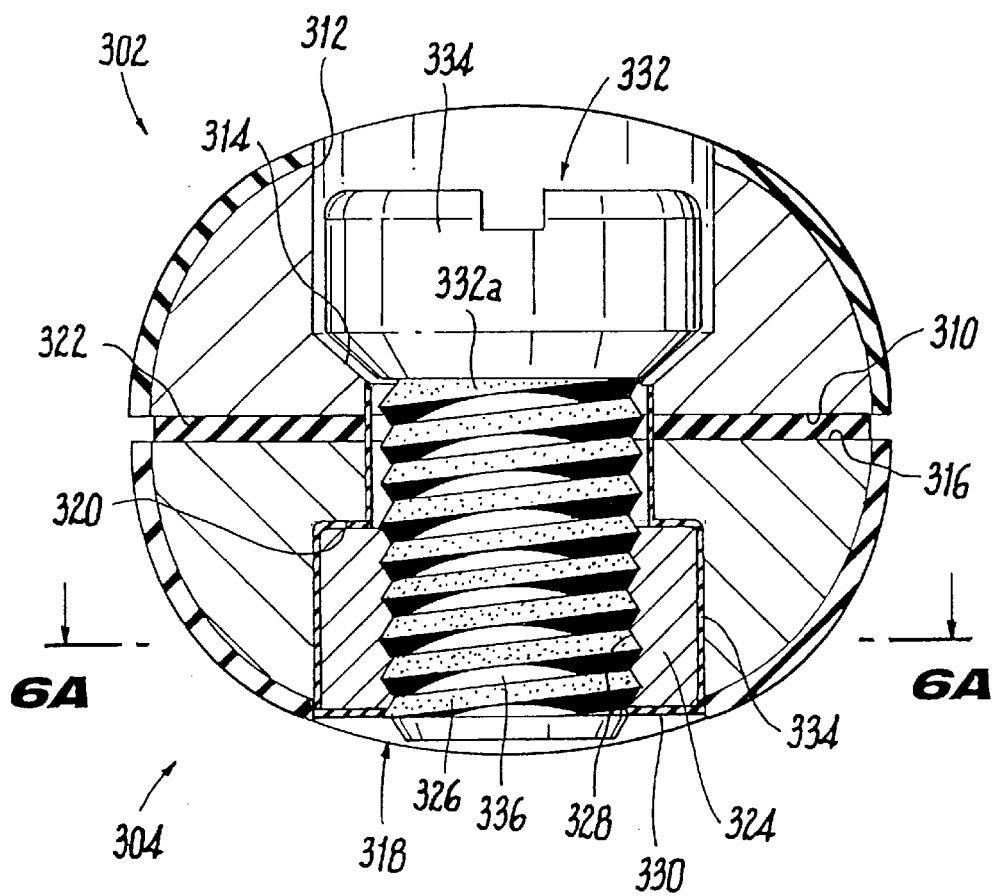
FIG. 4A illustrates a sectional view of a first embodiment of the bipolar electrosurgical instrument of FIG. 3 in which the pivot screw design comprises a single insert, the sectional view being taken along line 4A—4A.

Referring now in detail to FIGS. 3 and 4A, there is illustrated a first embodiment of the inventive bipolar electrosurgical instrument having an improved pivot screw design, and generally referred to by reference numeral 300. The bipolar electrosurgical instrument 300 has a first half 302 and a second half 304. The first and second halves 302, 304 each having a distal 302a,304a and a proximal 302b, 304b end. In the configuration illustrated in FIG. 3, the instrument 300 is configured as a scissor having first and second scissor portions 306,308 disposed at the distal ends 302a,304a of the first and second halves 302,304, respectively. The scissor portions 306,308 are disposed such that they are in cooperation with each other to provide cutting and coagulation of tissue and severed blood vessels. However, it is understood by someone skilled in the art that the instrument can be configured as any type of bipolar instrument (e.g., forceps, dissectors) without departing from the spirit and scope of the invention.

The first half 302 comprises a first electrode of a first polarity and has a first pivot surface 310 and a first bore 312. The first bore 312 has a first stepped portion 314. The second half 304 similarly comprises a second electrode of a second polarity and has a second pivot surface 316 in sliding contact with the first pivot surface 310 and a second bore 318 having a second stepped portion 320. The second bore 318 is aligned (i.e., shares the same center) with the first bore 312.

An insulating material 322 is disposed on one of the first and second pivot surfaces 310,316 for electrically isolating the first half 302 from the second half 304. The insulating material 322 is preferably aluminum oxide deposited on the first pivot surface 310 by any vapor deposition process known in the art. Alternatively, the insulating material 322 can be a thin sheet of insulating material, such as aluminum oxide or silicon nitride bonded to the first pivoting surface 310 using a suitable adhesive, such as an epoxy adhesive.

Figure 6A:
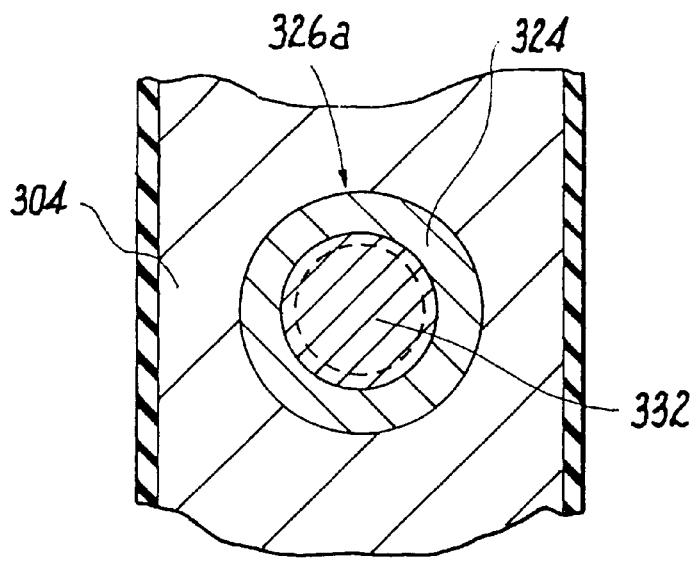
FIG. 6A illustrates a sectional view of the insert as taken along line 6A—6A in FIG. 4A.
Figure 6B:
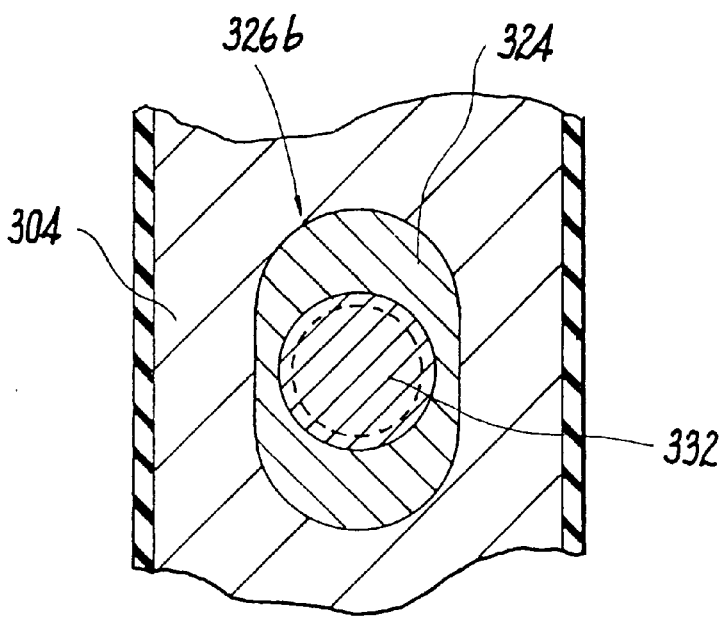
FIG. 6B illustrates a sectional view of an alternative insert as it would appear if taken along line 6A—6A in FIG. 4A.

Also provided in the instrument 300 is an insert 324 having a cross-sectional profile. The insert 324 is disposed in the second bore 318 and prevented from entering the first bore 312 by the second stepped portion 320. As can be seen in FIGS. 6A and 6B the cross-sectional profile of the insert 324 can take on any shape. The cross-sectional profile of the insert 324 can be round 326a as is shown in FIG. 6A. However, the cross-sectional profile of the insert 324 is preferably a shape other than round such that the insert 324 is prevented from rotating in the second bore 318 which has a similar cross-sectional profile for acceptance of the insert 324. Preferably, the cross-sectional profile of the insert 324 is elliptical 326b as is shown in FIG. 6B.

Referring back to FIGS. 3 and 4A, a third bore 326 is provided in insert 324 which has portions defining first threads 328. A first insulating coating 330 is disposed on all surface portions of the insert 324, including the portions defining the first threads 330. Also provided is a pivot screw 332 having a head 334 and portions defining a second thread 336. The pivot screw 332 is disposed in the first and second bores 312,318 such that the head 334 is prevented from entering the second bore 318 by the first stepped portion 314 and where the portions defining the second thread 336 pass through the first and second bores 312,318 into the third bore 326 and engage with the first thread 328. This arrangement fastens the first half 302 to the second half 304 such that sliding contact exists along the first and second pivot surfaces 310,316.

The insert 324 is typically held in place in the second bore 318 by any fastening means known in the art, such as by mating threads on the insert 324 exterior and second bore 318 interior, or by being press fit into the second bore 324. Preferably, the fastening means is an epoxy 334 that is preferably an electrical insulator, such as EP42HT by Masterbond Inc. The epoxy 334 adds another electrical insulating layer between the first and second halves 302,304 via the pivot screw 332 and the insert 324 in addition to the first insulating coating 330. The first insulating coating 330 is typically an anodized coating. If epoxy 334 is used as the fastening means for fastening the insert 324 in the second bore 318, then the anodized coatings that comprise the first insulating coating 330 is preferably a hard anodization without any polymer impregnation, such as the Hardtuf® anodized coating offered by Tiodize Inc. This type of anodized coating offers greater adhesion between the epoxy 334 and the anodized coatings because the epoxy 334 is able to infiltrate the micro-porosity of the anodized surface.

The pivot screw 332 is typically fabricated from a metal, such as an aluminum alloy and preferably is coated with a fourth electrically insulating coating 332a on all its surface portions, including the portions defining the second thread 336. Typical insulating coatings include anodized coatings and ceramic coatings such as aluminum oxide. Although not preferred, the pivot screw 332 can also be fabricated entirely from a non-conducting material, such as a ceramic or a thermoplastic, preferably a high strength thermoplastic such as polyetheretherketone (PEEK) available from ICI Americas, Inc. under the trade name of VICTREX®.

The operation of the arrangement of elements 30 in the first embodiment of the present invention as illustrated in FIG. 4A will now be described. The first and second halves 302,304 are electrically isolated from each other by the insulating material 322 disposed between the first and second pivot surfaces 310,316. The insulating material 322 acts as an insulating barrier to any current conduction between the halves. However, there is also a potential current path between the instrument halves via the pivot screw 332. Further insulation protection over the first embodiment is achieved by the first insulating coating 330 on the insert 324. Alternatively, still further insulative protection is achieved with a second insulating coating 332a disposed on the pivot screw 332 and the insulating epoxy 334 disposed between the insert 324 and the second bore 318. The insulating scheme of the first embodiment greatly decreases the possibility of an electrical short between the first and second instrument halves 302,304.

Figure 4B:
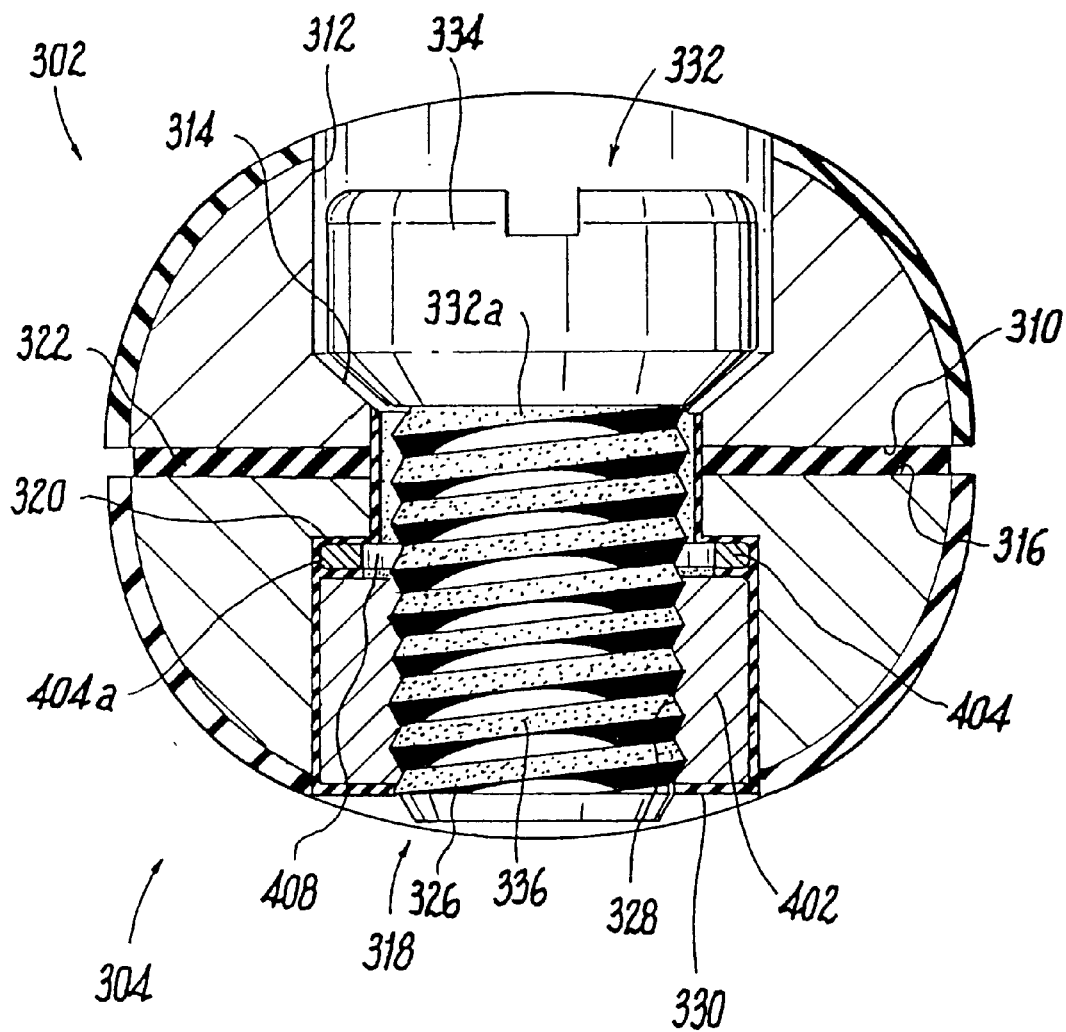
FIG. 4B illustrates a sectional view of a variation of the first embodiment of the bipolar 10 electrosurgical instrument of FIG. 3 in which the pivot screw design comprises two inserts, the sectional view being as it would appear if taken along line 4A—4A.

A variation of the first embodiment illustrated in FIG. 4B of the drawings in which all components similar to or identical with those in FIG. 4A are designated with the same reference numerals, is merely modified with regard to the first embodiment, in that the insert 324 is now referred to as a first insert 402 and a second insert 404 has been added in the second bore 318, disposed between the first insert 402 and the second stepped portion 320.

Referring now in detail to FIG. 4B, there is illustrated the inventive bipolar electrosurgical instrument 300 having a variation of the pivot screw design illustrated in FIG. 4A. The bipolar electrosurgical instrument has a first half 302 and a second half 304. The first and second halves 302,304 each having a distal 302a,304a and a proximal 302b,304b end. The first half comprises a first electrode of a first polarity and has a first pivot surface 310 and a first bore 312. The first bore 312 has a first stepped portion 314. The second half 304 similarly comprises a second electrode of a second polarity and has a second pivot surface 316 in sliding contact with the first pivot surface 310 and a second bore 318 having a second stepped portion 320. The second bore 318 is aligned with the first bore.

An insulating material 322 is disposed on one of the first and second pivot surfaces 310,316 for electrically isolating the first half 302 from the second half 304. As discussed previously, the insulating material 322 is preferably aluminum oxide deposited on the first pivot surface 310 by any vapor deposition process known in the art.

The insert 324 of the first embodiment is now referred to as a first insert 402. Like the insert 324, the first insert 402 has a cross-sectional profile, now referred to as a first cross-sectional profile. As discussed previously and illustrated in FIGS. 6A and 6B, the first cross-sectional profile of the first insert 402 can take on any shape. The cross-sectional profile of the first insert 402 can be round 326a as is shown in FIG. 6A. Alternatively, the cross-sectional profile of the first insert 402 can be a shape other than round such that it is prevented from rotating in the second bore 318 which has a similar cross-sectional profile for acceptance of the first insert 402. If the cross-sectional profile of the first insert 402 is other than round, it is preferred that it be elliptical 326b as is shown in FIG. 6B.

Referring back to FIG. 4B, a third bore 326 is provided in the first insert 402. The third bore 326 has portions defining first threads 328. A first insulating coating 330 is disposed on all surface portions of the first insert 402, including the portions defining the first threads.

A second insert 404 having a second cross-sectional profile, a second insulating coating 406, and a fourth bore 408 is also provided. The second insert 404 is disposed in the second bore 318 between the second stepped portion 320 and the first insert 402. Both the first and second inserts 402,404 are prevented from entering the first bore 312 by the second stepped portion 320. Like the first insert, the cross-sectional profile of the second insert 404 can take on any shape, and can alternatively be other than round, such as elliptical, to prevent it from rotating in the second bore 318, which is of a similar cross-sectional profile, as is the cross-sectional profile of the first insert 402.

A pivot screw 322 having a head 334 and portions defining a second thread 336 is disposed in the first, second, and third bores 312,318,326 such that the head 334 is prevented from entering the second bore 318 by the first stepped portion 314 and where the portions defining the second thread 336 pass through the first, second, and fourth bores, 312,318,408 into the third bore 326 where it engages with the first thread 328 whereby the first half 302 is fastened to the second half 304 for sliding contact therewith along the first and second pivot surfaces 310,316. As discussed with regard to the previous embodiment, the pivot screw 322 preferably has an insulating coating 322a or can be made entirely from a non-conducting material.

The operation of the arrangement of elements in the variation of the first embodiment of the present invention as illustrated in FIG. 4B will now be described. In the variation of the first embodiment of the present invention the alternative current path between the instrument halves via the pivot screw 332 is further fortified by the existence of the second insert 404. In addition to the electrical insulation offered as discussed with regard to the first embodiment, the second insert 404 combats another potential current path encountered in practice. Upon torquing the pivot screw 332 into the first insert 402, if not for the second insert 404, the first insert 402 would bear up against the edges of the second stepped portion 320. The contact between the first insert 402 and the second stepped portion 320 (which is typically fabricated from a relatively hard material such as stainless steel) tends to pierce the first insulating coating 330 on the first insert 402 creating a conductive path between instrument halves. The second insert 404 is disposed between the first insert 402 and the second stepped portion 320 such that the edges of the second stepped portion 320 do not contact either the first or second inserts 402,404. Thus, the edges of the second stepped portion 320 cannot pierce the first insulating coating 330 and no conductive path is created. The insulating scheme of the variation of the first embodiment further decreases the possibility of an electrical short between the first and second instrument halves 302,304. The second insert 404 is preferably fabricated from aluminum, and coated with an insulating coating 404a. The insulating coating 404a is preferably an anodized layer.

Figure 5A:
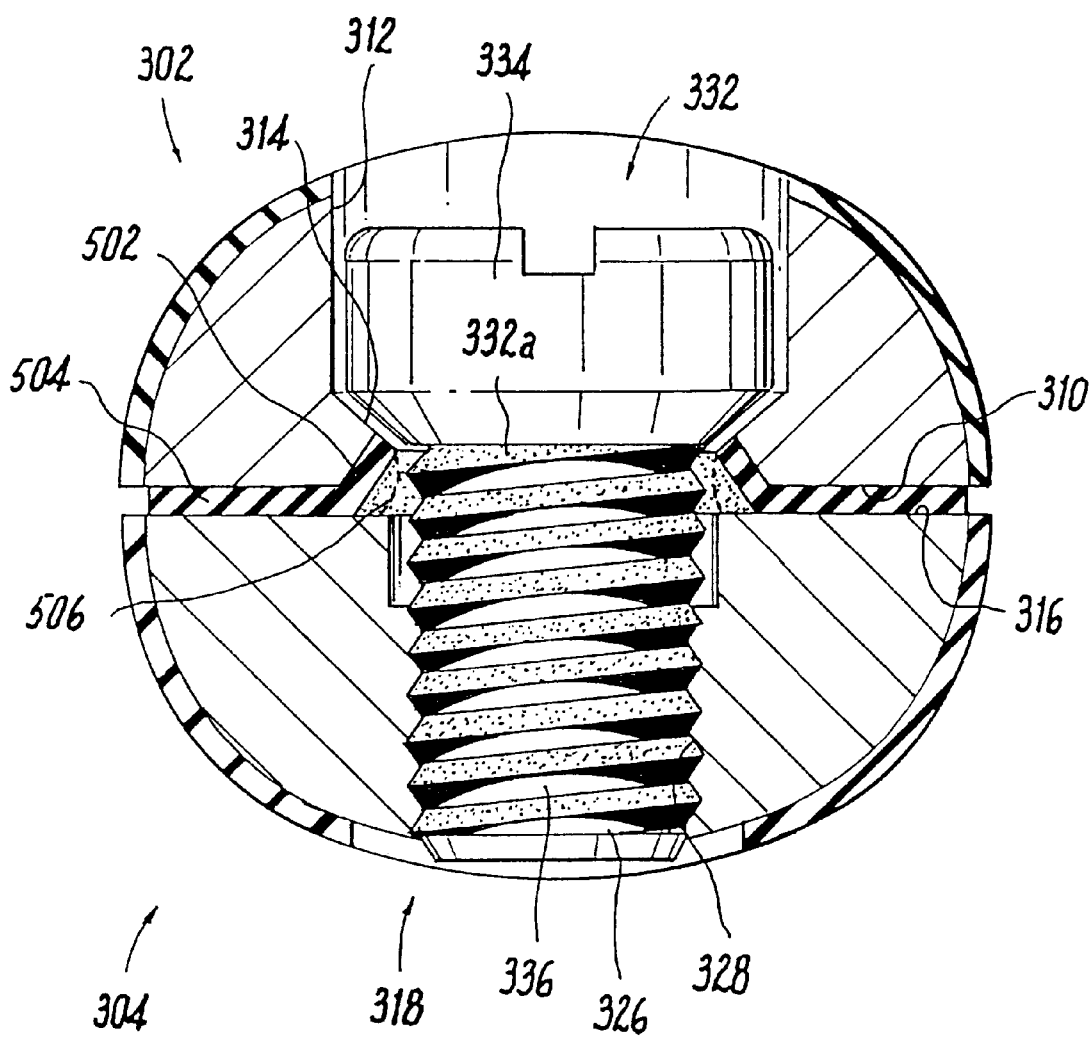
FIG. 5A illustrates a sectional view of a it second embodiment of the bipolar electrosurgical instrument of FIG. 3 in which the pivot screw design comprises a chamfered elongated portion having an extended insulating material, the sectional view being as it would appear if taken along line 4A—4A.

A second embodiment illustrated in FIG. 5A of the drawings in which all components similar to or identical with those in FIGS. 4A and 4B are designated with the same reference numerals, is merely modified with regard to the first embodiment, and variation thereof, in that first and second inserts 402,404 are eliminated from the design and in which an elongated portion 502 exists in the first bore 312.

Referring now in detail to FIG. 5A, there is illustrated the inventive bipolar electrosurgical instrument 300 having an improved pivot screw design of a second embodiment. Like the first embodiment, and variation thereof, the second embodiment of the present invention has a first half 302 and a second half 304. The first and second halves 302,304 each having a distal 302a,304a and a proximal 302b,304b end. The first half comprises a first electrode of a first polarity and has a first pivot surface 310 and a first bore 312. The first bore 312 has a first stepped portion 314. However, the first bore 312 also has an elongated portion 502 proximate to the first pivot surface 310. The elongated portion 502 is an extension of the first pivot surface 310 and is typically a chamfer on the side of the first bore 312 proximate to the first pivot surface 310. However, the elongated portion can be shaped in any way which elongates or extends the surface of the first pivot surface 310, such as a radius 502a as shown in FIG. 5D.

Referring back to FIG. 5A, the second half 304 comprises a second electrode of a second polarity and has a second pivot surface 316 in sliding contact with the first pivot surface 310 and a second bore 318 having a second stepped portion 320. The second bore 318 has a first thread 328 and is aligned with the first bore.

In the second embodiment, the insulating material 322 is disposed on the first pivot surface 310 and extended onto the elongated portion 502, the extended insulating material now referred to by reference numeral 504. Like the first embodiment, the extended insulating material 504 is for electrically isolating the first half 302 from the second half 304 but also acts to increase the length of the possible conductive path, shown as dashed line 506, between the first and second halves. This increase in the length of the conductive path 506 leads to an increase in resistance across the path and a decrease in voltage drop because of the short caused by the path. Thus, the possibility of a depreciable decrease in the hemostasis capability of the instrument is minimized.

Lastly, a pivot screw 332 having a head 334 and portions defining a second thread 336 is disposed in the first and second bores 312,318 such that the head 334 is prevented from entering the second bore 318 by the first stepped portion 314 and where the second thread 336 passes through the first and second bores 312,318 engaging with the first thread 328 whereby the first half 302 is fastened to the second half 304 for sliding contact therewith along the first and second pivot surfaces 310,316. As discussed with regard to the previous embodiments, the pivot screw 322 preferably has an insulating coating 322a or can be made entirely from a non-conducting material.

Figure 5B:
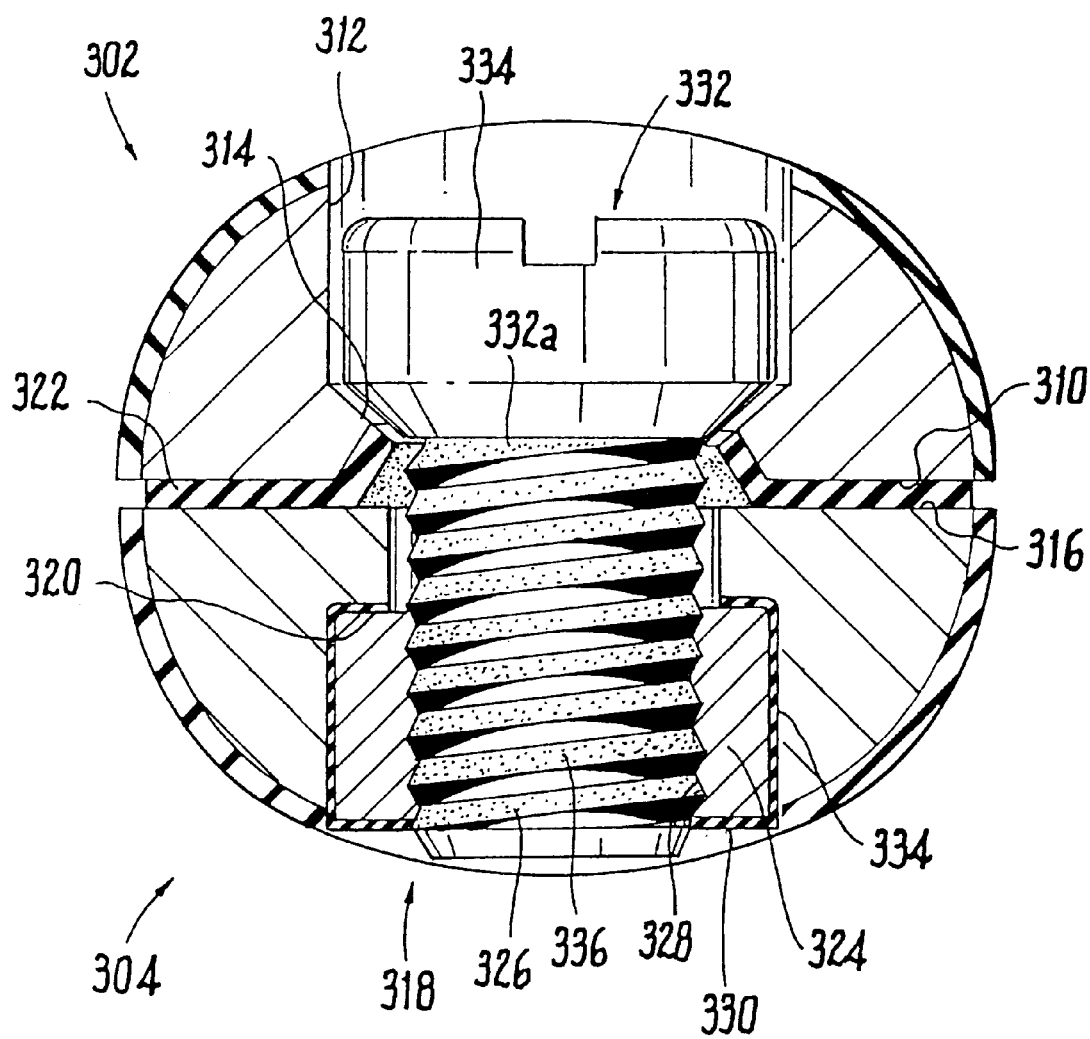
FIG. 5B illustrates a sectional view of a first variation of the second embodiment of the bipolar electrosurgical instrument of FIG. 3 in which the pivot screw design comprises a chamfered elongated portion having an extended insulating material and a single insert, the sectional view being as it would appear if taken along line 4A—4A.
Figure 5C:
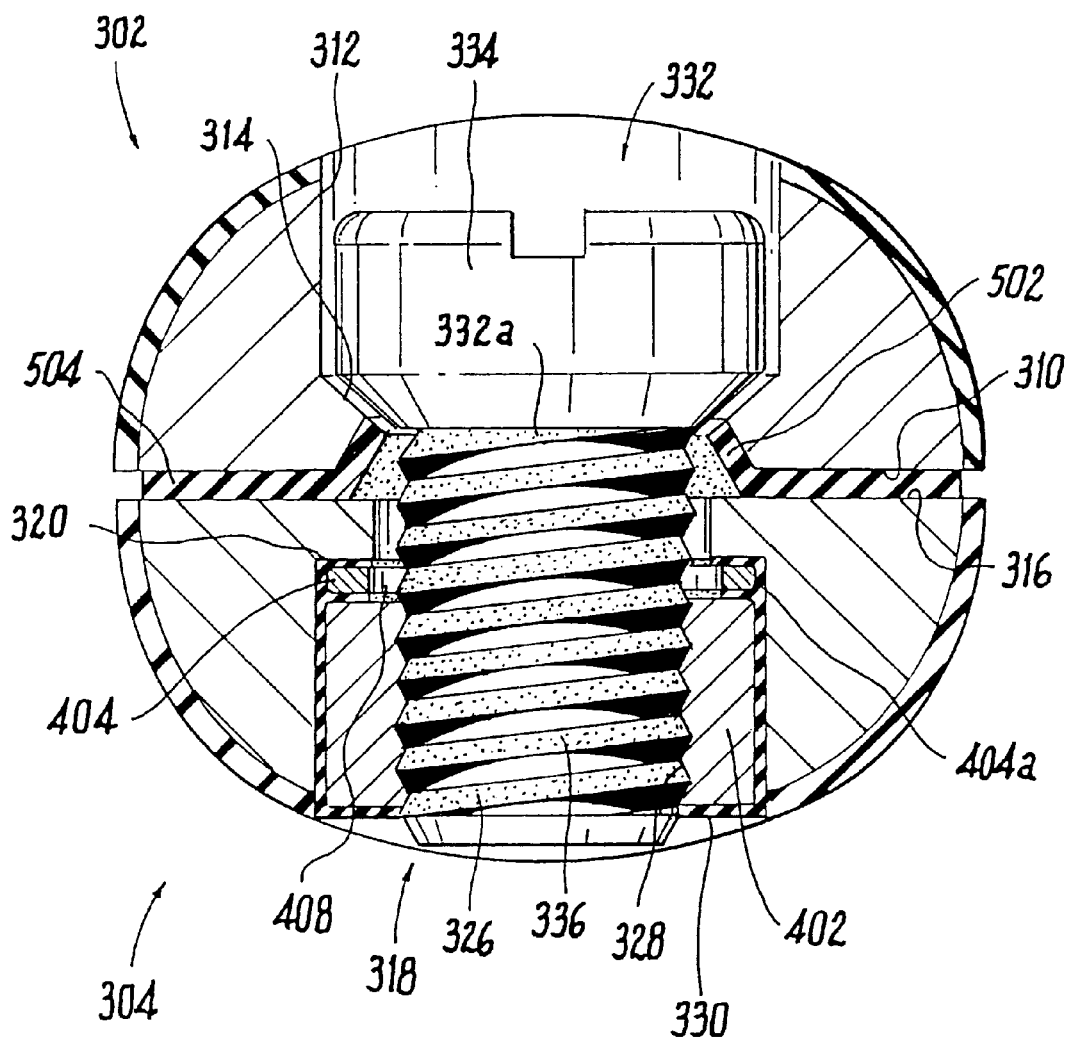
FIG. 5C illustrates a sectional view of a second variation of the second embodiment of the bipolar electrosurgical instrument of FIG. 3 in which the pivot screw design comprises a chamfered elongated portion having an extended insulating material and two inserts, the sectional view being as it would appear if taken along line 4A—4A.
Figure 5D:
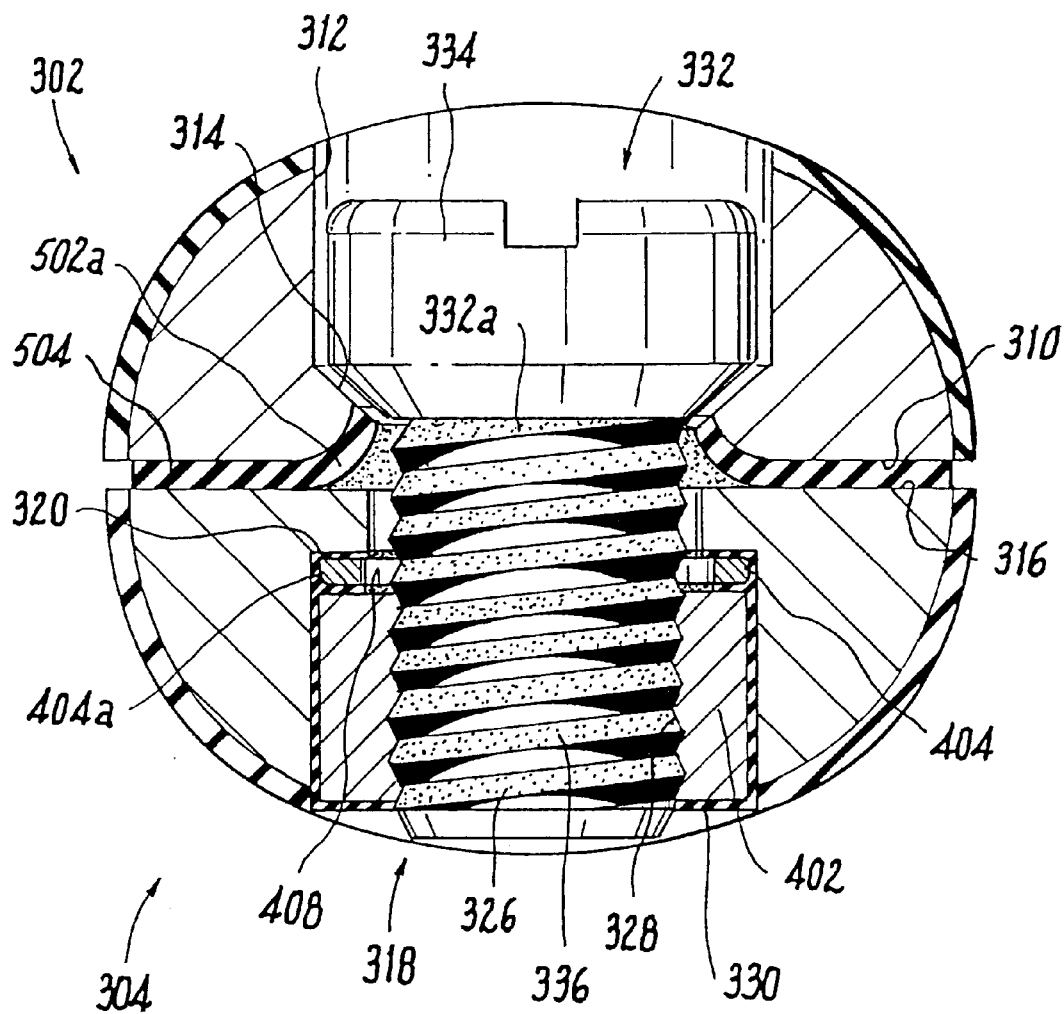
FIG. 5D illustrates a sectional view of a third variation of the second embodiment of the bipolar electrosurgical instrument of FIG. 3 in which the pivot screw design comprises a radiused elongated portion having an extended insulating material, the sectional view being as it would appear if taken along line 4A—4A.

First and second variations of the second embodiment illustrated in FIGS. 5B and 5C of the drawings in which all components similar to or identical with those in FIGS. 4A, 4B and 5A are designated with the same reference numerals, is merely modified with regard to the second embodiment, in that the second embodiment is combined with the first embodiment and variation thereof, respectively. Thus, the insulating benefits of the first and second embodiments, and variations thereof, are also combined to result in a bipolar electrosurgical instrument which greatly reduces the possibility of a short between the instrument halves.

From the foregoing, it becomes readily apparent to one skilled in the art that the novel pivot screw design provides for increased safety, and efficiency by decreasing the likelihood that poor hemostasis will result from worn or chipped insulation of the pivot screw thread and/or its mating thread and/or chipped portions of the insulating material disposed between instrument halves.

Although this invention has been shown and described with respect to detailed embodiments thereof, it will be understood by those skilled in the art that various changes in form and detail thereof may be made without departing from the spirit and scope of the claimed invention.

What is claimed is:

1. A bipolar electrosurgical instrument having an improved pivot screw design, the bipolar electrosurgical instrument comprising:

a first half comprising a first electrode of a first polarity, the first half having a first pivot surface and a first bore, the first bore having a stepped portion, an elongated portion proximate to the first pivot surface;

a second half comprising a second electrode of a second polarity, the second half having a second pivot surface in sliding contact with the first pivot surface and a second bore having a first thread, the second bore being aligned with the first bore;

an insulating material disposed on the first pivot surface and the elongated portion of the first bore for electrically isolating the first half from the second half and for increasing the length of the possible conductive path between the first and second halves; and a pivot screw having a head and a second thread, the pivot screw being disposed in the first and second bores such that the head is prevented from entering the second bore by the first stepped portion and where the second thread passes through the first and second bores engaging with the first thread whereby the first half is fastened to the second half for sliding contact therewith along the first and second pivot surfaces.

2. The bipolar electrosurgical instrument of claim 1, wherein the elongated portion of the first bore is a chamfer.

3. The bipolar electrosurgical instrument of claim 1, wherein the elongated portion of the first bore is a radius.

4. The bipolar electrosurgical instrument of claim 1, further comprising first and second scissor portions disposed on the first and second halves respectively, the scissor portions being in cooperation with each other to provide cutting and cauterization of tissue.

5. The bipolar electrosurgical instrument of claim 1, wherein the insulating material is aluminum oxide.

6. The bipolar electrosurgical instrument of claim 1, wherein the screw is fabricated from a thermoplastic material.

7. The bipolar electrosurgical instrument of claim 6, wherein the thermoplastic is polyetheretherketone.

8. The bipolar electrosurgical instrument of claim 1, further comprising a first insulating coating disposed on the pivot screw to provide further isolation between the first and second instrument halves.

9. The bipolar electrosurgical instrument of claim 8, wherein the first insulating coating is an anodized coating.

10. The bipolar electrosurgical instrument of claim 9, wherein the first insulating coating is aluminum oxide.

* * * * *